United States Patent [19]

Samuelsson et al.

[11] 3,984,458

[45] Oct. 5, 1976

[54] 4,5-CIS-DIDEHYDRO-PGB₁ COMPOUNDS

[75] Inventors: Bengt Samuelsson, Stockholm, Sweden; Barney J. Magerlein, Portage, Mich.

[73] Assignee: The Upjohn Company, Kalamazoo, Mich.

[22] Filed: Sept. 9, 1975

[21] Appl. No.: 611,790

Related U.S. Application Data

[60] Division of Ser. No. 440,628, Feb. 7, 1974, which is a continuation of Ser. No. 248,005, April 27, 1972, abandoned.

[52] U.S. Cl. .......................... 260/468 D; 260/488 R; 260/514 D
[51] Int. Cl.² ..................................... C07C 177/00
[58] Field of Search ............... 260/468 D, 514 D, 69

[56] References Cited
OTHER PUBLICATIONS

Van Dorp, Annals N.Y. Acad. of Sciences, 180, 181, (1971).

*Primary Examiner*—Robert Gerstl
*Attorney, Agent, or Firm*—Morris L Nielsen

[57] ABSTRACT

This invention is a group of 4,5-didehydro and 4,5,17,18-tetradehydro PG₁ (prostaglandin-type) compounds, and processes for making them. These compounds are useful for a variety of pharmacological purposes, including anti-ulcer, inhibition of platelet aggregation, increase of nasal patency, labor inducement at term, and wound healing.

11 Claims, No Drawings

4,5-CIS-DIDEHYDRO-PGB₁ COMPOUNDS

This is a division of application Ser. No. 440,628, filed Feb. 7, 1974, which is a continuation of Ser. No. 248,005, filed Apr. 27, 1972, now abandoned.

BACKGROUND OF THE INVENTION

This invention relates to novel compositions of matter, to novel methods for producing them, and to novel chemical intermediates useful in those processes. Particularly, this invention relates to certain novel analogs of some of the known prostaglandins in which a cis carbon-carbon double bond links C-4 and C-5 in the carboxy-terminated chain.

The essential material for this application, including the background of the invention, the disclosure of the invention, and the description of the preferred embodiments, including Preparations and Examples, is incorporated by reference from U.S. Patent No. 3,954,835, columns 1–30, inclusive, under the provisions of M.P.E.P. 608.01(p).

4,5-Didenydro-PGE₁ mentioned in the prior art (see van Dorp, Annals N.Y. Acad. Sci. vol. 180, page 181, esp. pp. 184–185, 1971).

SUMMARY OF THE INVENTION

It is a purpose of this invention to provide novel prostaglandin analogs in which a cis carbon-carbon double bond links C-4 and C-5 in the carboxy-terminated chain. It is a further purpose to provide esters, lower alkanoates, and pharmacologically acceptable salts of said analogs. It is a further purpose to provide a novel process for preparing said acids and esters. It is still a further purpose to provide novel intermediates useful in said process.

The presently described acids and esters of the 4,5-unsaturated prostaglandin analogs include compounds of the following formulas, and also the racemic compounds of each respective formula and the mirror image thereof:

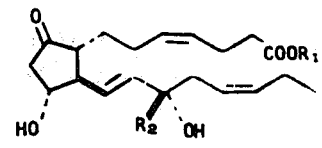 XII

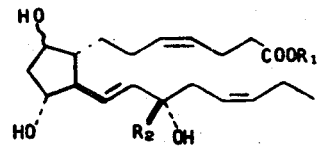 XIII

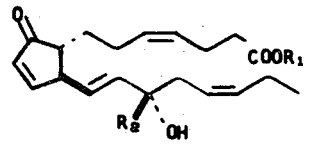 XIV

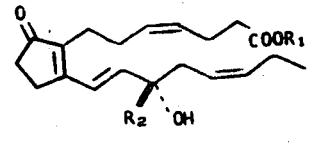 XV

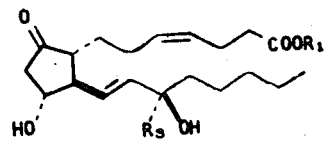 XVI

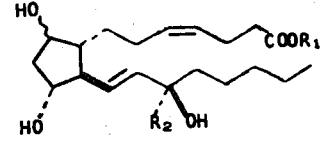 XVII

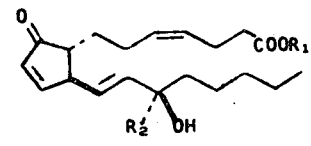 XVIII

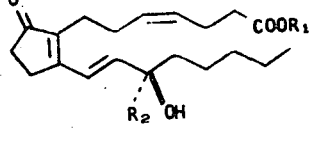 XIX

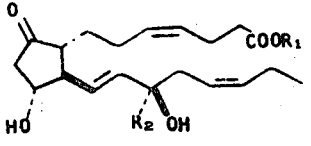 XX

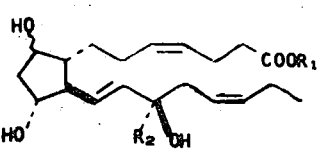 XXI

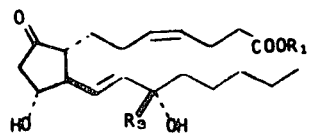 VIII

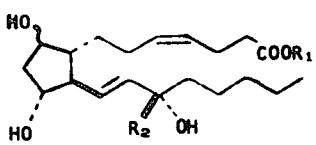 IX

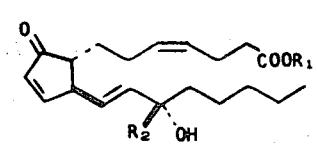 X

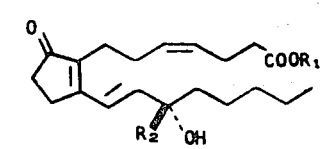 XI

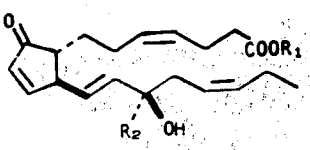

XXII

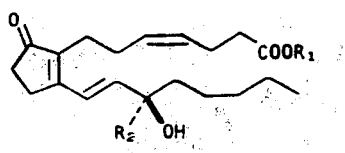

XXIII

In Formulas VIII to XXIII, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive: $R_2$ is hydrogen, methyl, or ethyl: $R_3$ is methyl or ethyl; and the wavy line ~ indicates attachment to the cyclopentane ring in alpha or beta configuration.

Formula IX represents 4,5-cis-didehydro-PGF$_{1\alpha}$ when $R_1$ and $R_2$ are hydrogen and ~ indicates the alpha configuration. Formula XII represents 4,5-cis-17,18-cis-tetradehydro-PGE$_1$ when $R_1$ and $R_2$ are hydrogen. Formula XVII represents 4,5-cis-didehydro-15$\beta$-PGF$_{1\beta}$, methyl ester, when $R_1$ is methyl, $R_2$ is hydrogen, and ~ indicates the beta configuration.

As in the case of formulas II to VII, formulas VIII to XV are each intended to represent optically active prostanoic acid derivatives with the same absolute configuration as PGE$_1$ obtained from mammalian tissues. Furthermore, formulas VIII to XV represent compounds having the S configuration at C-15, i.e. wherein the hydroxyl is attached to the side chain in alpha configuration. Also included within this invention are the 15-epimer compounds corresponding to

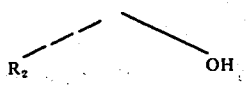

of formulas XVI to XXIII wherein the C-15 hydroxyl is in R (beta) configuration. Hereinafter, "15$\beta$" refers to the epimeric configuration. Thus, "4,5-cis-didehydro-15$\beta$-PGE$_{1\alpha}$" identifies a compound of formula XVII, similar to that of formula IX except that it has the beta (or R) configuration at C-15 instead of the natural alpha (or S) configuration of 4,5-cis-didehydro-PGF$_{1\alpha}$. Each of formulas VIII to XV plus its mirror image describe a racemic compound within the scope of this invention; likewise each of the 15-epimer formulas corresponding to formulas XVI to XXIII plus its mirror image describe a racemic compound within the scope of this invention. For convenience hereinafter, such a racemic compound is designated by the prefix "racemic" (or "dl") before its name; when that prefix is absent, the intent is to designate an optically active compound represented by the appropriate formula VIII to XXIII.

With regard to formulas VIII to XXIII, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2',2-dimethylcyclopropyl, 2,3-diethylcyclopropyl, 2-butylcyclopropyl, cyclobutyl, 2-methylcyclobutyl, 2-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclododecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

We claim:
1. An optically active compound of the formula

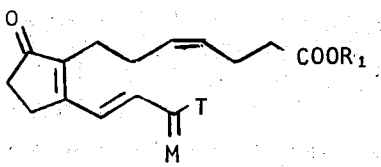

or a racemic compound of that formula and the mirror image thereof, wherein M is

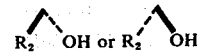

wherein $R_2$ is hydrogen, methyl, or ethyl; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein T is 1-pentyl or cis 1-pent-2enyl; including the lower alkanoates thereof, and the pharmacologically acceptable salts thereof when $R_1$ is hydrogen.

2. A compound according to claim 1 wherein T is 1-pentyl.

3. 4,5-cis-Didehydro-PGB$_1$, a compound according to claim 2.

4. 4,5-cis-Didehydro-PGB$_1$, methyl ester, a compound according to claim 2.

5. 15(S)-15-Methyl-4,5-cis-didehydro-PGB$_1$, a compound according to claim 2.

6. 15(S)-15-Methyl-4,5-cis-didehydro-PGB$_1$, methyl ester, a compound according to claim 2.

7. 15(R)-15-Methyl-4,5-cis-didehydro-PGB$_1$, methyl ester, a compound according to claim 2.

8. 15(R)-15-Methyl-4,5-cis-didehydro-PGB$_1$, methyl ester, a compound according to claim 2.

9. A compound according to claim 1 wherein T is cis 1-pent-2-enyl.

10. 4,5-cis-17,18-cis-Tetradehydro-PGB$_1$, a compound according to claim 9.

11. 4,5-cis-17,18-cis-Tetradehydro-PGB$_1$, methyl ester, a compound according to claim 9.

* * * * *

UNITED STATES PATENT OFFICE
CERTIFICATE OF CORRECTION

Patent No. 3,984,458   Dated October 5, 1976

Inventor(s) Bengt Samuelsson et al.

It is certified that error appears in the above-identified patent and that said Letters Patent are hereby corrected as shown below:

Column 1, line 23, "Didenydro-" should read -- Didehydro- --.
Column 3, line 48, "$PGE_{1\alpha}$" should read -- $PGF_{1\alpha}$ --. Column 4, line 9, "cyclododecyl" should read -- cyclodecyl --.

Signed and Sealed this

First Day of March 1977

[SEAL]

Attest:

RUTH C. MASON
Attesting Officer

C. MARSHALL DANN
Commissioner of Patents and Trademarks